United States Patent [19]
Wieczorek

[11] Patent Number: 5,708,490
[45] Date of Patent: Jan. 13, 1998

[54] GOGGLES FOR USE WITH LASER PROJECTION ASSEMBLY SYSTEMS

[75] Inventor: John P. Wieczorek, Waterloo, Canada

[73] Assignee: Virtek Vision Corp., Waterloo, Canada

[21] Appl. No.: 593,818

[22] Filed: Jan. 30, 1996

[51] Int. Cl.[6] .................................. G02C 9/00; G02C 7/10
[52] U.S. Cl. ............................. 351/47; 351/165; 2/8
[58] Field of Search ........................... 351/44, 47, 158, 351/163, 165; 2/7, 8

[56] References Cited

U.S. PATENT DOCUMENTS

| | | | |
|---|---|---|---|
| 3,791,721 | 2/1974 | Helfrich | 351/44 |
| 4,039,254 | 8/1977 | Harsch | 359/63 |
| 4,071,912 | 2/1978 | Budmiger | 2/8 |
| 4,241,286 | 12/1980 | Gordon | 219/147 |
| 4,462,661 | 7/1984 | Witt | 351/158 |
| 4,511,225 | 4/1985 | Lipson | 351/49 |
| 4,547,909 | 10/1985 | Bell | 351/158 |
| 4,703,522 | 11/1987 | Schurle et al. | 351/44 |
| 4,826,286 | 5/1989 | Thornton, Jr. | 351/44 |
| 4,863,244 | 9/1989 | Fuerthbauer et al. | 2/8 |
| 4,978,208 | 12/1990 | Hsu et al. | 351/45 |
| 5,146,623 | 9/1992 | Paysan et al. | 351/44 |
| 5,170,501 | 12/1992 | White | 2/8 |

Primary Examiner—Huy Mai
Attorney, Agent, or Firm—Howard & Howard

[57] ABSTRACT

Improved goggles for use with laser projection systems allow passage of a narrow band of red wavelengths that surround the wavelength at which the laser is projecting. The goggles block adjacent wavelengths. Thus, the laser image is in contrast, and is easily seen by a wearer. At the same time, the goggles pass at least a portion of the blue and green wavelengths. Thus, the wearer is provided with an image that is not unnatural, but includes most of the natural colors. In this way, the goggles not only provide a clear image of the laser beam, but also are easily worn by a wearer for an extended period of time.

20 Claims, 1 Drawing Sheet

GOGGLES FOR USE WITH LASER PROJECTION ASSEMBLY SYSTEMS

BACKGROUND OF THE INVENTION

This invention relates to a unique pair of goggles that provide a worker with an enhanced view of a laser projection beam.

In the prior art, laser projectors are utilized to assist industrial and construction operations. As one example, lasers have been utilized to provide an outline of desired positions for truss components. The laser provides an outline of the connection points for the separate wooden members that make up the truss. An assembler then either places holding structure, or the actual truss components on the connection points. The truss is then assembled based upon the connection points. Other common uses for laser projection including alignment of lamina, nesting of parts to be cut from a sheet, and many other applications.

A laser beam is almost universally generated in a single wavelength. Laser projector systems are utilized in combination with galvanometers, and move the beam rapidly about a work surface to give the appearance of a two-dimensional image. In the above described truss application, the laser projection system rapidly moves the beam and provides an outline of the position for parts to be assembled.

The operations assisted by the laser beam may take place in ambient light that washes out the laser image. Thus, an assembler working near the laser image may have some difficulty in seeing the laser image, and assembling parts with the image. The problem is more pronounced when assembly occurs outside, but also applies during inside assembly.

In the past, laser goggles have been proposed to assist an assembler in seeing the beam. The goggles filter out a range of light wavelengths, and are intended to improve the visibility of the laser beam. The prior art laser goggles have typically filtered out all visible light except in the red range. The goggles are for use with a red laser. Thus, the assembler is provided with a viewing image that includes no blue or green visible wavelengths, but all the red wavelengths.

With the prior art goggles, the laser image is still washed out by the surrounding red wavelengths. Moreover, it is quite unpleasant for the assembler to wear these goggles for any extended period of time. Since the goggles limit vision to only red wavelengths, a user becomes uncomfortable after wearing the goggles for any extended period of time.

SUMMARY OF THE INVENTION

In a disclosed embodiment of this invention, goggles for use by a worker who must view a laser image filter most of the red wavelengths surrounding a narrow band. The narrow band surrounds the wavelength at which the laser is projecting. In addition, the filter preferably passes at least a portion of the blue and green wavelengths such that a more natural view is provided to a worker. Since most red wavelengths are removed, the laser image stands in stark contrast to the blue and green wavelengths which are allowed to pass. Thus, the laser beam is more visible. At the same time by providing at least a portion of all colors, a more natural image is provided, such that the worker may comfortably wear the goggles for an extended period of time.

In preferred embodiments of this invention, the goggles pass a greater percentage of the narrow band than passed in the blue and green wavelengths. As an example, the blue and green wavelengths may be only passed at approximately 5% of the intensity, while the laser may be passed at an amount over 50% of its intensity. The narrow band of red is over a very small range of wavelengths. On the other hand, the blue and green wavelengths that will be passed are over a much wider band of wavelengths. The lower transmittance of the blue and green wavelengths serves to balance the amount of blue and green relative to the red to result in a more natural total visual image.

The narrow laser wavelength band may extend for approximately 15 nm. The transmission of other red wavelengths adjacent to that band is minimized.

In a method of utilizing the inventive goggles, filters that remove most of the red wavelengths surrounding a narrow band but passes a portion of the green and blue wavelengths and placed between a worker and a laser image. In this way, the worker is able to easily see the projected laser image and perform work guided by the laser image.

Although this application is directed to a red laser, a similar goggle could be designed for other color lasers. Those goggles would still remove bands on either side of a narrow band associated with the laser generation wavelength. Preferably, those goggles would also pass the majority of the wavelengths in the remainder of the visual spectrum to provide the more natural total visual image.

These and other features of the present invention will be best understood from the following specification and drawings, of which the following is a brief description.

DETAILED DESCRIPTION OF PREFERRED EMBODIMENT

Figure 1:
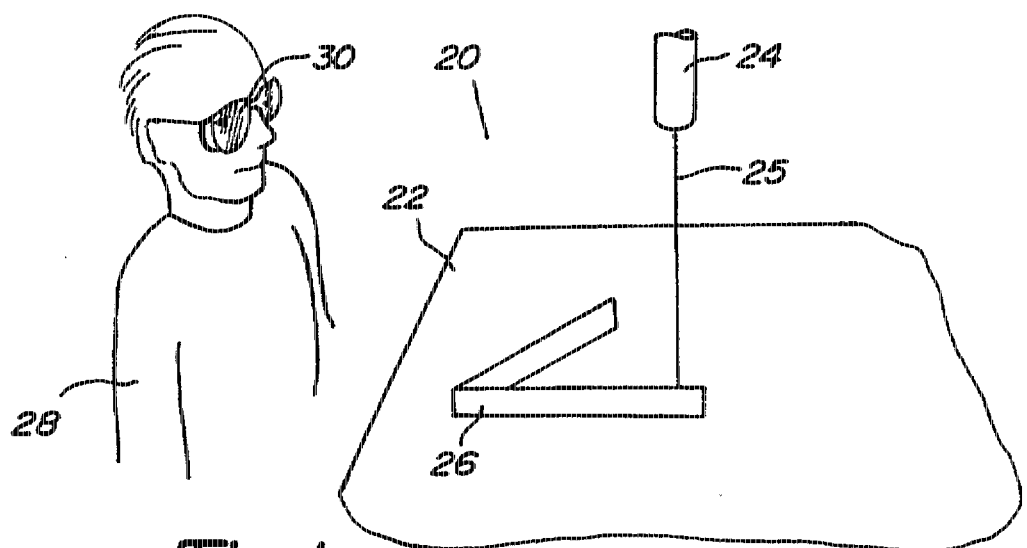
FIG. 1 is a schematic view showing a worker in a laser assembly application.

A system 20 for projecting a laser image onto a work surface 22 is shown in FIG. 1. The laser projector system 24 incorporates a laser generator and a galvanometer system as is known in the prior art. Suitable systems are described, as an example, in U.S. Pat. No. 5,381,258. A beam 25 is directed from system 24 onto the work surface 22 as is known in the art. The beam 25 moves quickly such that an image 26 appears to a worker 28. Worker 28 is wearing the inventive goggles 30. By utilizing the inventive goggles, the image 26 stands in stark contrast to the surrounding work surface 22, and the worker 28 is able to easily see the image 26.

Figure 2:
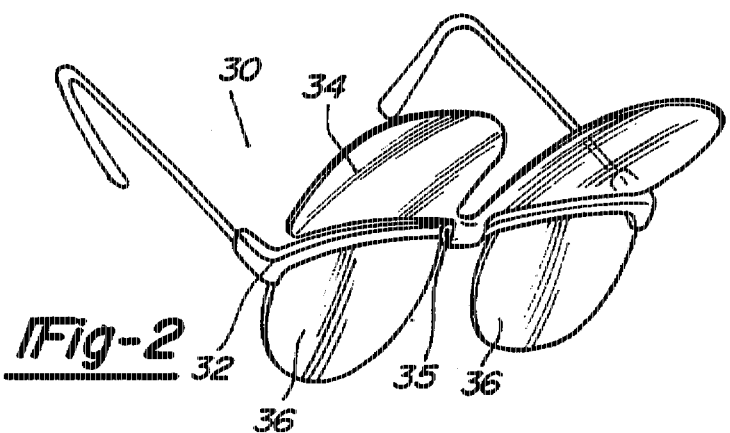
FIG. 2 shows a pair of goggles carrying the inventive filters.

As shown in FIG. 2, the goggles 30 include a glasses frame portion 32, and flip-up filters 34. Thus, the worker 28 may flip up the filters 34 when they are not being utilized. A hinge 35 is shown, but any known flip-up structure may be utilized. One main benefit of the inventive goggles 30 is that they are easier for a worker to wear than the prior art goggles. The flip-up filters 34 increase this benefit. Although the filters 34 are shown as being approximately the same size as the underlying non-filtering lenses 36 of the goggle 30, it may be desirable that the filters 34 be made smaller than the lenses 36.

Figure 3:
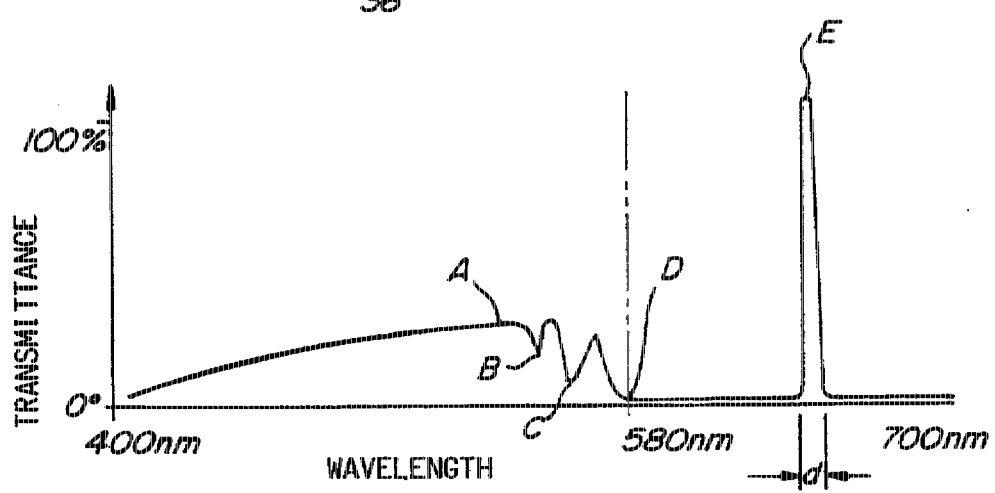
FIG. 3 is a graph showing the transmittance versus wavelengths for the filters shown in FIG. 2.

As shown in FIG. 3, the filters 34 are designed to allow transmission of a small amount of the blue and green wavelengths typically found approximately between 400 and 580 nm. In one actual production filter, the end of the passed wavelengths in the blue and green spectrum actually occurred closer to 520 nm. There is no bright line distinction between the several colors, and instead the colors tend to blend together into the secondary colors between the primary colors. As such, this application does not attempt to establish bright line distinctions, but rather refers to "the majority of the wavelengths" in certain areas and there respective colors as being passed or removed as required.

As shown at Point A, the transmittance may be on the order of approximately 5% of the intensity of the light in those wavelengths. The transmittance is defined as the percentage of the intensity of the light passed through the filters compared to the intensity of the light in the particular wavelength. Valleys such as shown at Points B and C exist where the transmittance drops down. The valleys are not a design feature, but rather are believed to be an expected result of current filter technology near the break point between the transmitted blue and green wavelengths and the beginning of the non-transmitted red wavelengths.

Eventually, the transmittance drops down to Point D, which is selected to be near the beginning of the red wavelengths. As can be seen in FIG. 3, at least a portion of the majority of the wavelengths between 400 and 580 nm. is passed through the filters 34. Point D preferably passes approximately zero percent of the wavelengths in the area before between the beginning of the red wavelengths, or approximately 580 nm., and the beginning of the narrow band. Again, in one production goggle, point D occurred at 520 nm. Obviously, a filter which passes a small percentage of the intensity in this area would still come within the scope of this invention.

FIG. 3 is the currently preferred filter characteristics. It should be understood the main goal of this invention is to provide contrast about the narrow red band, and further to provide some blue and green wavelengths to the viewer. For that reason, the main features of this invention could be characterized as passing a first transmittance level of the narrow band, only passing a second transmittance level of wavelengths on either side of the narrow band, with the second transmittance level being lower than the first transmittance level. In a second feature, passing a third transmittance level of the majority of the wavelengths and the blue and green spectrum, with the third transmittance level being higher than the second transmittance level. Also, as can be seen, the third transmittance level is preferably lower than the first transmittance level. As explained above, this serves to balance the combined green and blue wavelengths with the narrow band of red wavelengths. Since so many more wavelengths of blue and green are transmitted, if those wavelengths were transmitted at a higher level there might be an imbalance between the blue and green and the narrow band red that would result in a poorer image of the laser.

It should also be understood when considering this invention that making the second transmittance level of the wavelengths on either side of the narrow band to be something other than zero, but still relatively small, would not avoid the teachings of this invention. It is believed that such a filter would be inferior to the preferred filter shown in FIG. 3, wherein the wavelengths on either side of the narrow band are fully blocked, however, such a filter would still come within the scope of this invention. Similarly, the claims typically refer to the majority of the wavelengths in the respective areas described above. This not only accounts for the peaks and valleys such as shown at Points B and C on FIG. 3, but also should make clear that this invention would extend to filters that might have a designed high transmittance or low transmittance blip or peak in one of these areas over a small number of wavelengths. Further, by referring to the majority of the wavelengths, the claims recognize that there are no bright line distinctions between the colors, and thus the boundaries of each of the sections may vary. As an example, while FIG. 3 shows the end of the blue and green wavelengths as occurring at approximately 580 nm, in one pair of production goggles, point D occurred at 520 nm.

Point E is the wavelength at which the laser beam is generated. In one example, that wavelength may be 632.8 nm. Point E is in a band associated with the wavelength of the laser beam 25. The band and Point E show a peak transmittance at 90% of the intensity of the light at those wavelengths. The band providing Point E may extend for a small width d. In this example, the band is selected to be approximately 15 nm wide. In practice, it is preferred that the band be less than 30 nm. It is important to narrowly design this band specific to the wavelength of the laser. The contrast between the laser beam wavelength, and the other removed wavelengths around the beam provides the improved visibility of the projected image. The narrower the band, the starker the contrast.

The filters 34 could be summarized as allowing the majority of the blue and green wavelengths to pass at a limited transmittance. Preferably, that limited transmittance is less than the transmittance of the narrow beam, such as identified by Point E. The filters 34 remove the bulk of the red wavelengths around the narrow band about Point E. In this way, the inventive filters 34 provide a worker 28 with the ability to clearly see the contrasted image 26 on the work surface 22. By passing the blue and green wavelengths, the worker is still able to view the work surface 22 for an extended period of time without eyesight strain. The blue and green wavelengths also make the image easier to view than the prior art "red" goggles.

Again, while the specific disclosed embodiment for these goggles is for use with a red laser, the teachings of this invention would extend to other color lasers. In those other goggles, a narrow band surrounding the laser would still be passed, and bands defined on either side of that narrow band would be blocked. The remainder of the visual spectrum outside of those blocked areas would be passed at a level which is preferably lower that the level of the narrow transmission band, but still higher than the level at which the blocked band are transmitted.

The filter may be achieved by any known optical filter technology. In one preferred embodiment, the red wavelengths were filtered using an interference filter of the sort having precision controlled thicknesses of various optic media having different refractive indices. Typically, such filters would include an additional glass filter layer to provide the blue and green transmittance as described above. Again, the teachings of this invention relate in general to the respective transmittance levels disclosed in this application. A small blip within one of the three main types of transmittances described in this application does not avoid the teachings of this invention. Moreover, as can be seen in FIG. 3, the transmittance is not defined by solid lines. Rather, the narrow band curves upward at a very high slope to a curved peak. The curved peak is preferably selected to be at the wavelength of the laser. The blue and green wavelengths curve upward at a much lower slope to their transmittance peaks. That is, the transmittance levels in each of the bands are not constant, but do vary across their bands.

As can be seen in the preferred embodiment shown in FIG. 3, the filters do block out at least a portion of the intensity of all of the wavelengths. In describing the function of the filters, the description and Claims herein may refer to blocking certain wavelengths or allowing passage of certain wavelengths. These are relative terms in that the filters block all wavelengths somewhat.

Although a preferred embodiment of this invention has been disclosed, a worker of ordinary skill in the art would recognize that certain modifications would come within the scope of this invention. For that reason, the following claims should be studied to determine the true scope and content of this invention.

I claim:

1. Goggles for use in viewing projected laser images comprising:

a frame for being worn by a wearer; and a filter placed on said frame, said filter passing a first transmittance level of light in a narrow band of wavelengths adjacent to and including a projection wavelength of a laser to be utilized with said goggles, said filter passing a second transmittance level of light wavelengths within a preselected bandwidth adjacent to either side of said narrow band, and passing a third transmittance level of light at wavelengths outside of said narrow band and said preselected bandwidth, said first transmittance level being substantially greater than said third level and said third level being higher than said second level such that a user is able to view a projected laser image when wearing said goggles because said first transmittance level allows the projected image to be seen while the second transmittance level effectively blocks transmittance at said adjacent wavelengths to thereby enhance the viewability of the projected image.

2. Goggles as recited in claim 1, wherein said laser is a red laser, and said outside wavelengths are in the blue and green visual spectrum and are generally defined by wavelengths between 400 and 580 nm, said filter passing at least a portion of said wavelengths between 400 and 580 nm.

3. Goggles as recited in claim 2, wherein said second level is approximately zero.

4. Goggles as recited in claim 2, wherein said third level is less than 50% of the intensity of said outside wavelengths wherein said outside wavelengths range between 400 and 580 nm.

5. Goggles as recited in claim 1, wherein said first transmittance level is approximately 100%.

6. Goggles as recited in claim 5, wherein said third transmittance level is less than 10%.

7. Goggles as recited in claim 1, wherein said first level of transmittance is greater than 50%.

8. Goggles as recited in claim 7, wherein the second level of transmittance is less than 10%.

9. Goggles as recited in claim 8, wherein said second level is approximately zero percent transmittance.

10. Goggles as recited in claim 1, wherein said narrow band is less than 30 nm.

11. Goggles as recited in claim 10, wherein said narrow band is approximately 15 nm.

12. Goggles as recited in claim 1, wherein at least one of said transmittance levels is not uniform.

13. A method of utilizing a pair of goggles for viewing a laser projected image comprising the steps of:

(1) providing a filter designed to pass a first transmittance level of light within a narrow band of wavelengths including a wavelength associated with said laser, a second transmittance level of wavelengths within a preselected bandwidth adjacent to said narrow band, and allow passage of a third transmittance level of light at wavelengths outside of said narrow band and said preselected bandwidth, said first and third levels being higher than said second level;

(2) generating a laser image at a wavelength within said narrow band; and (3) placing said filter between a worker and a laser image such that the worker is able to see the laser image without distortion of the image otherwise caused by light within said preselected bandwidth, and performing work based upon a laser image.

14. A method as recited in claim 13, wherein said third transmittance level is less than 10%.

15. A method as recited in claim 13, wherein said filter is connected to a frame of a pair of goggles.

16. A method as recited in claim 13, wherein said laser is generated in a red wavelength within said narrow band, said preselected bandwidth includes red wavelengths, and said outside wavelengths from step (1) are within the blue and green visual spectrum.

17. Goggles for use with a laser assembly guidance system comprising:

filters to be placed over a wearer's eyes, said filters passing a narrow band of red wavelengths at a first transmittance level, said narrow band being selected to include the wavelength of the laser to be utilized with said filters, said narrow band extending for less than 30 nm, and said filters passing wavelengths within a preselected bandwidth on either side of said narrow band at a second transmittance level which is substantially less than said first transmittance level such that a user is able to view a projected laser image when wearing said goggles because said first transmittance level allows the projected image to be seen while the second transmittance level effectively blocks transmittance at said adjacent wavelengths to thereby enhance the viewability of the projected image.

18. Goggles as recited in claim 17, wherein said filters pass wavelengths in the blue and green visual spectrum that are outside of said narrow band and said preselected bandwidth at a third transmittance level that is higher than said second transmittance level.

19. Goggles as recited in claim 18, wherein said first transmittance level is greater than 50%.

20. Goggles as recited in claim 19, wherein said third level of transmittance is less than 10%.

* * * * *